(12) United States Patent
Zhang et al.

(10) Patent No.: US 7,317,188 B2
(45) Date of Patent: Jan. 8, 2008

(54) TEM SAMPLE PREPARATION FROM A CIRCUIT LAYER STRUCTURE

(75) Inventors: Wen Yi Zhang, Singapore (SG); Weng Yee Kwong, Singapore (SG)

(73) Assignee: Systems On Silicon Manufacturing Company Pte. Ltd., Singapore (SG)

( * ) Notice: Subject to any disclaimer, the term of this patent is extended or adjusted under 35 U.S.C. 154(b) by 253 days.

(21) Appl. No.: 11/115,410

(22) Filed: Apr. 27, 2005

(65) Prior Publication Data

US 2006/0243919 A1    Nov. 2, 2006

(51) Int. Cl.
*G01N 23/00* (2006.01)
(52) U.S. Cl. ............... 250/307; 250/311; 250/492.21; 315/382; 430/5
(58) Field of Classification Search ........... 250/307
See application file for complete search history.

(56) References Cited

U.S. PATENT DOCUMENTS

| | | | |
|---|---|---|---|
| 5,104,684 A | | 4/1992 | Tao et al. |
| 6,368,753 B1 | * | 4/2002 | Harriott et al. ............... 430/5 |
| 6,664,552 B2 | * | 12/2003 | Shichi et al. ........... 250/492.21 |
| 6,693,290 B2 | | 2/2004 | Yamaguchi |
| 6,753,538 B2 | | 6/2004 | Musil et al. |
| 6,943,507 B2 | * | 9/2005 | Winkler et al. ............. 315/382 |
| 7,180,061 B2 | * | 2/2007 | Lu ............................ 250/307 |

* cited by examiner

*Primary Examiner*—David Vanore
(74) *Attorney, Agent, or Firm*—Rothwell, Figg, Ernst & Manbeck, PC

(57) ABSTRACT

A method of TEM sample preparation from a circuit layer structure, the method comprising electron-beam assisted deposition of a first protective layer over a site of interest of the circuit layer structure; ion-beam assisted deposition of a second protective layer over the first protective layer; and ion-beam milling at the site of interest through the first and second protective layers.

11 Claims, 12 Drawing Sheets

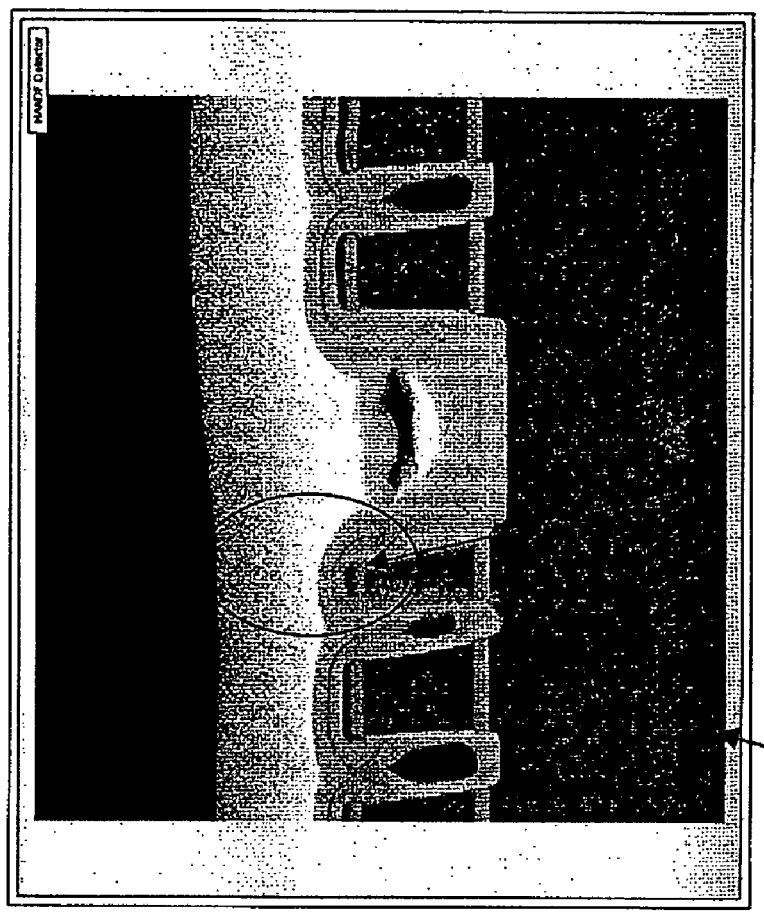
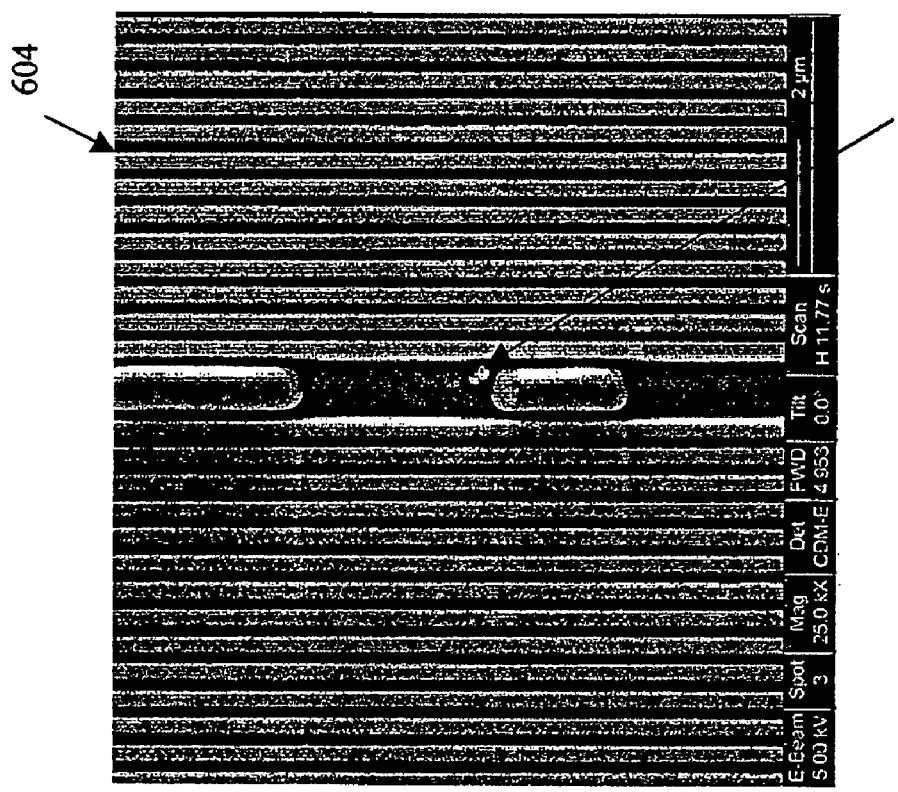
Fig. 6b
Fig. 6a

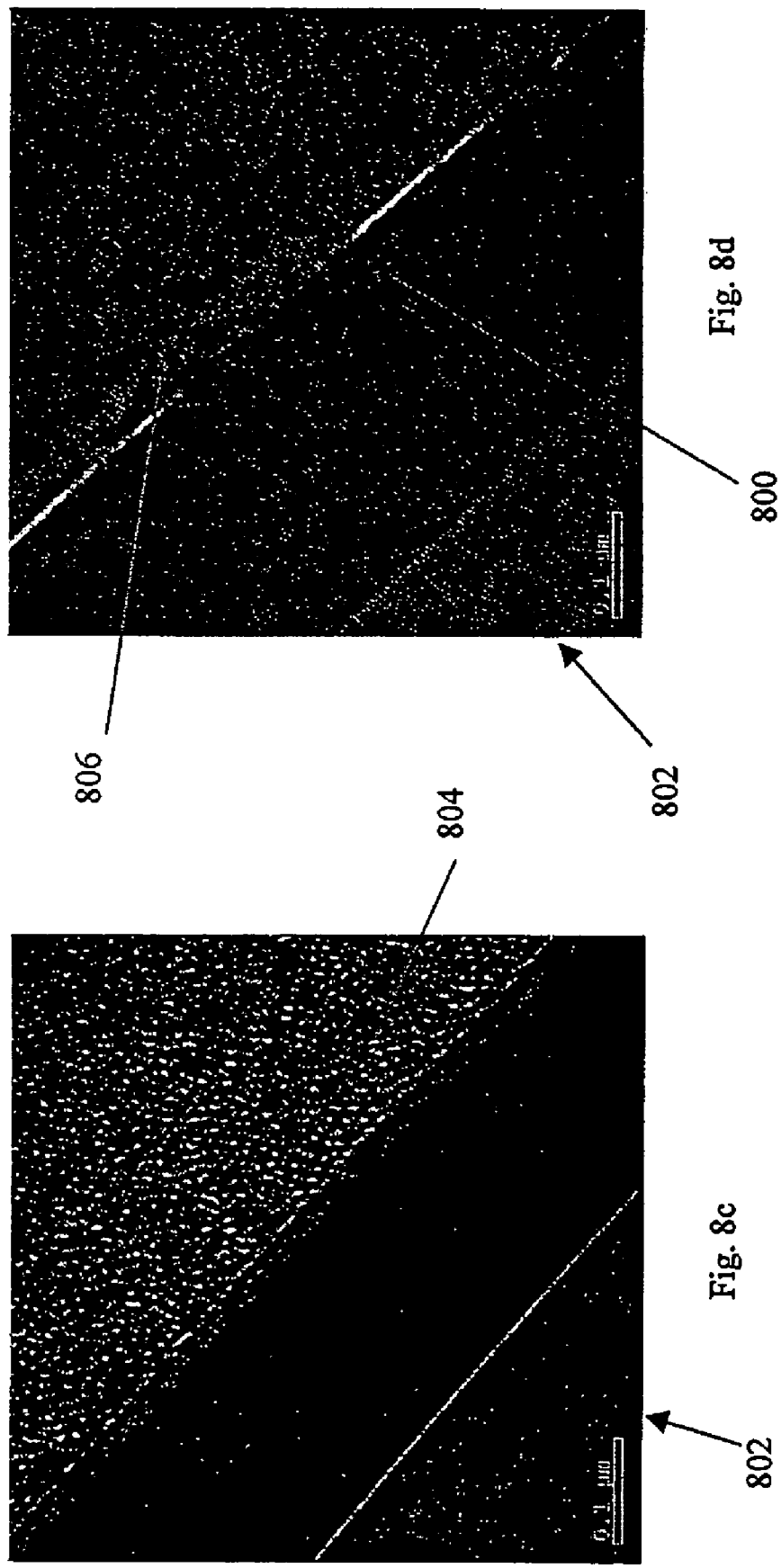

TEM SAMPLE PREPARATION FROM A CIRCUIT LAYER STRUCTURE

FIELD OF INVENTION

The present invention relates broadly to a method of TEM sample preparation from a circuit layer structure.

BACKGROUND

In circuit failure analysis, such as Ultra-Large Scale Integration (ULSI) circuit failure analysis, Transmission Electron Microscopes (TEMs) are typical tools that may be used. For preparation of TEM samples, the circuits for testing have to undergo localisation of the site of interest. The circuits typically comprise multi-layered structures on a wafer substrate.

TEM samples are typically prepared so that they may be viewed in either cross-sectional or planar-view orientations (where the orientations are with respect to the circuits).

For cross-sectional view TEM samples, localization of specific areas for TEM analysis is typically achieved with the use of a Scanning Electron Microscope (SEM) in a dual beam Focussed Ion Beam (FIB) system. As illustrated in FIG. 1, the SEM beam column (102) and a tilted FIB column (104) are calibrated and adjusted to "coincide" on a sample at a "coincidental" point (106). Using this technique, the specific area to be localised may be marked out by the SEM beam column (102) while the actual milling of the area to cut out the TEM sample may be conducted with the FIB column (104).

During TEM sample preparation, it is important to avoid or minimise any modification of the sample to be investigated. For example, it has been found that current TEM sample preparation processes have a low success rate in solving failure analysis cases related to small particles (<100 nm), metal/TiN stringer defects, or thin film analysis on wafers. Protective coatings are typically deposited over the site of interest using ion-beam assisted deposition of e.g. Platinum (Pt) to prevent features at the site of interest from being sputtered off during ion-beam milling to cut out the TEM samples. However, it has been found that during the ion-beam assisted deposition of the protective coating itself, damage may already have been done.

While it has been suggested to lower a current of the ion-beam during the deposition of the protective coating, some modification/damage of the site of interest is typically still observed, such as amorphorization.

SUMMARY

In accordance with an aspect of the present invention there is provided a method of TEM sample preparation from a circuit layer structure, the method comprising electron-beam assisted deposition of a first protective layer over a site of interest of the circuit layer structure; ion-beam assisted deposition of a second protective layer over the first protective layer; and ion-beam milling at the site of interest through the first and second protective layers.

The method may further comprise electron-beam assisted deposition of an intermediate protective layer over the first protective layer prior to the ion-beam assisted deposition of the second protective layer over the first and the intermediate protective layers.

The first and second protective layers may comprise Pt.

The first and second protective layers may be deposited from methylcyclopentadienyl (trimethyl) platinum $(CH_3C_5H_4)(CH_3)_3$ Pt.

The ion-beam may comprise Ga ions.

A Ga ion-beam acceleration voltage may be about 30 kV.

An electron-beam voltage may be in a range from about 2 to 5 kV.

An electron-beam spot size may be of the order of tens of nano metres.

An electron-beam assisted deposition time may be in a range from about 9 to 33 minutes.

A thickness of the first protective layer may be a range from about 0.036 to 0.7 micrometres, and a thickness of the second protective layer may be about 1 micrometre.

The method may further comprise tilting the circuit layer structure and performing a substantially U-shaped ion-beam milling to cut out the TEM sample, wherein dimensions of the substantially U-shaped ion-beam milling are chosen such that the ion-beam milling occurs away from the site of interest of the circuit layer structure.

BRIEF DESCRIPTION OF THE DRAWINGS

Embodiments of the invention will be better understood and readily apparent to one of ordinary skill in the art from the following written description, by way of example only, and in conjunction with the drawings, in which:

FIGS. 6a and b show TEM images illustrating avoidance of damage through utilising a protective layer structure according to an example embodiment.

FIG. 8a to d show images of a wafer under investigation, illustrating thin film analysis on wafers according to an example embodiment.

DETAILED DESCRIPTION

In an example embodiment, a TEM sample of a circuit layer structure can be prepared in a manner such that modification of the sample to be investigated is avoided or minimised. The TEM sample may be prepared in cross-sectional or planar view orientations.

Figure 1:
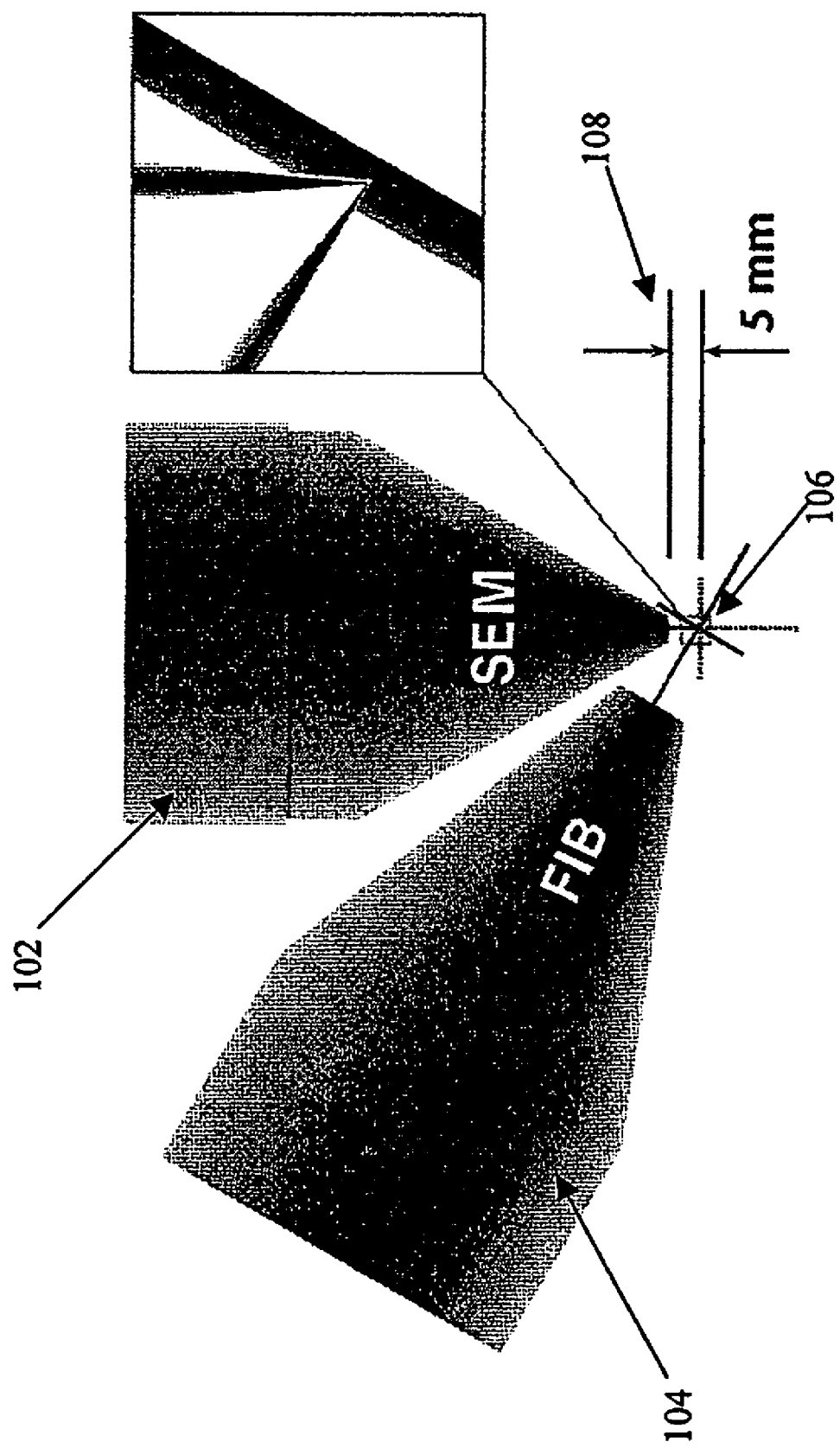
FIG. 1 is an illustration of a typical configuration of dual beam Focussed Ion Beam (FIB) system.
Figure 2:
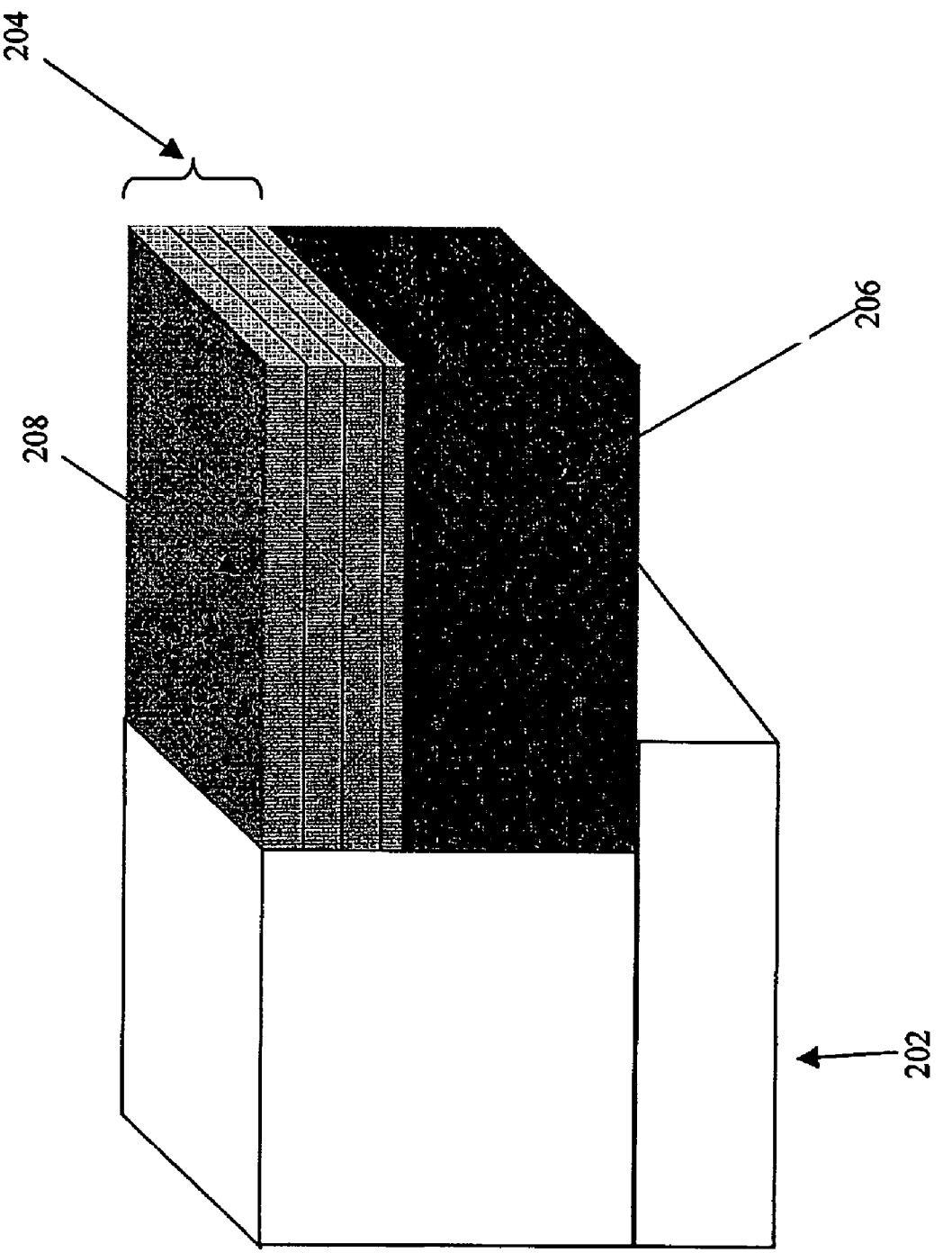
FIG. 2 is a schematic drawing of a substrate holder for use during a TEM sample preparation in an example embodiment.
Figure 2:
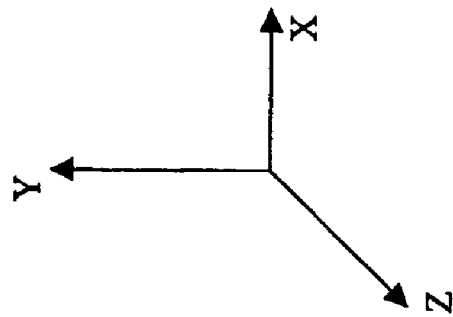

In the example embodiment, as illustrated in FIG. 2, a holder (202) is used to secure and keep in place circuit layers, for example (204), disposed on a substrate (206). The substrate (206) may be mounted on the holder (202) by way of a retaining material layer deposited around and above one end of the substrate (206) and a surface of the holder (202). The substrate (206) typically is a portion of a circuit layer wafer. The original wafer may e.g. be subject to cleaving, mechanical polishing, or both to a size of the substrate (206) suitable for introduction into a dual beam FIB system.

Figure 3A:
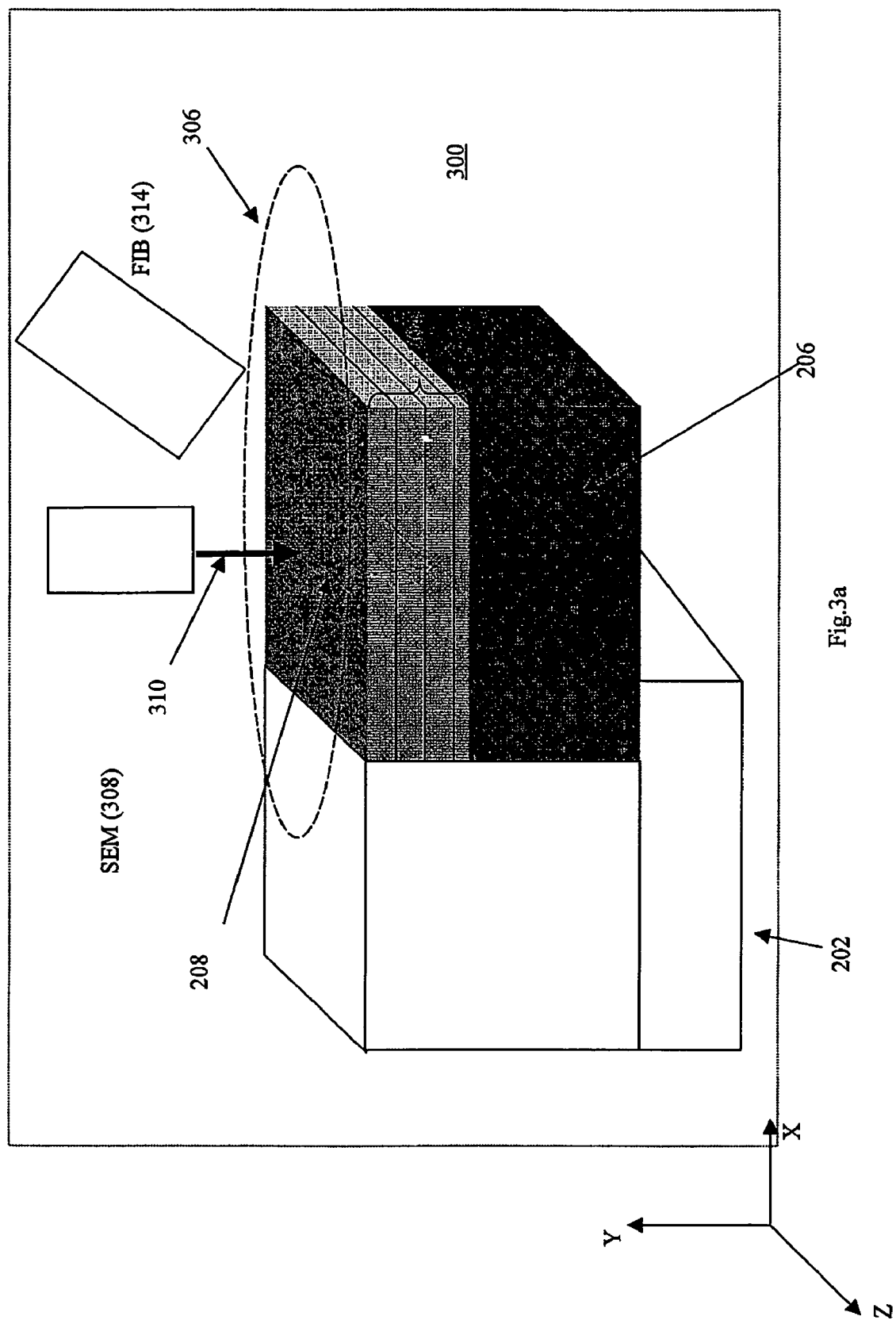
FIGS. 3a to c are schematic drawings illustrating the further processing steps in a TEM sample preparation according to an example embodiment.

With reference to FIG. 3a, in the example embodiment, the holder (202) is secured inside a dual beam FIB processing chamber (300) where FIB/SEM techniques are utilised for TEM sample preparation. The SEM (308) is utilised as a visual tool to view the site of interest (208) within the circuit layers (204).

In the example embodiment, electron beam induced deposition of a first protective layer over the site of interest (208) is performed. A Pt containing compound (306), in the example embodiment methylcyclopentadienyl (trimethyl) platinum ($CH_3C_5H_4$) ($CH_3$)$_3$ Pt is introduced into the processing chamber (300) at an ambient pressure of the order of $10^{-6}$ mbar. During the electron-beam assisted deposition of the first protective layer in the example embodiment, the Pt containing compound (306) is decomposed as a result of an interaction with electrons in the electron beam (310) on or at the surface of the site of interest (208), forming a first Pt protective layer.

Figure 3B:
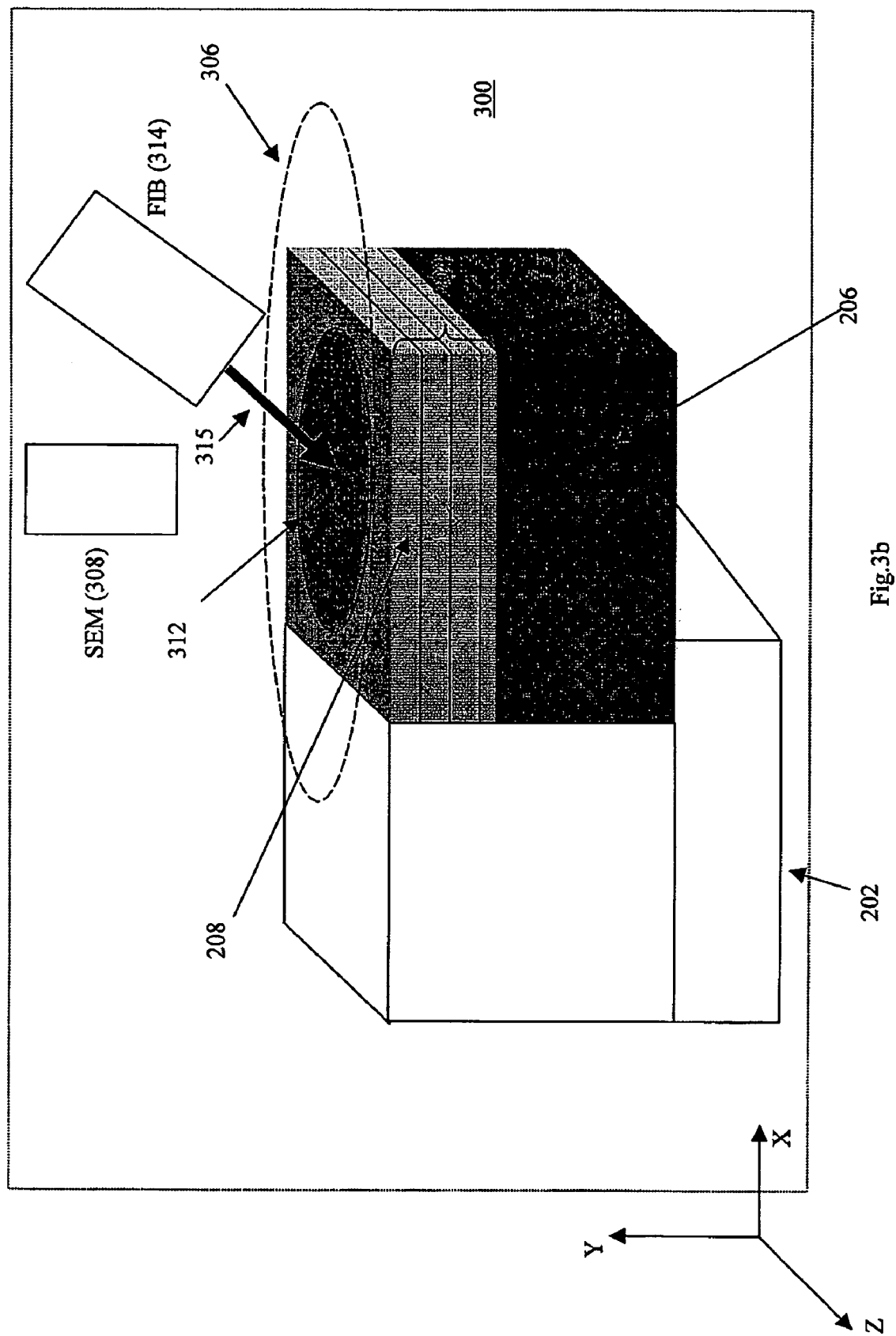

With reference to FIG. 3b, after the formation of the first Pt protective layer (312), the same Pt containing compound (306), in the example embodiment, is again introduced into the processing chamber (300) at an ambient pressure of the order of $10^{-6}$ mbar. In the example embodiment, Gallium (Ga) ion-beam deposition of a second Pt protective layer over the site of interest (208), including the first protective layer (312), is then performed using the FIB (314). During the ion-beam assisted deposition of the second Pt protective layer in the example embodiment, the Pt containing compound (313) is decomposed as a result of an interaction with the Ga ions in the ion-beam (315) on or at the surface of the first Pt protective layer (312).

In example embodiments the acceleration voltage of the Ga ion-beam is about 30 kV, and the electron-beam voltage is in a range from about 2 to 5 kV. The electron-beam spot size is of the order of tens of nano metres and an electron-beam assisted deposition time is in a range from about 9 to 33 minutes. A thickness of the first protective layer is a range from about 0.036 to 0.7 micro metres. A thickness of the second protective layer is about 1 micro metre in the example embodiment. The substrate (206) is kept at room temperature during both the electron-beam assisted and the ion-beam assisted deposition of the first and second protective layers respectively.

It was found that using the processing of the example embodiment described above with reference to FIGS. 3a and b, damage to the site of interest (208) can be avoided or minimised. More particular, the first protective layer (312) can be deposited using the electron-beam (310) in a manner such that damage to the site of interest (208) can be avoided, while at the same time providing a protective layer sufficient to further avoid any subsequent damage during deposition of the ion-beam deposited protective layer. In the example embodiment, a double-protective layer approach using electron-beam assisted deposition and ion-beam assisted deposition respectively can reduce overall processing time for deposition of a protective layer structure for avoiding damage during ion-beam milling for cutting out the TEM sample, compared with deposition of the entire protective layer structure utilising the electron-beam (310).

Figure 3C:
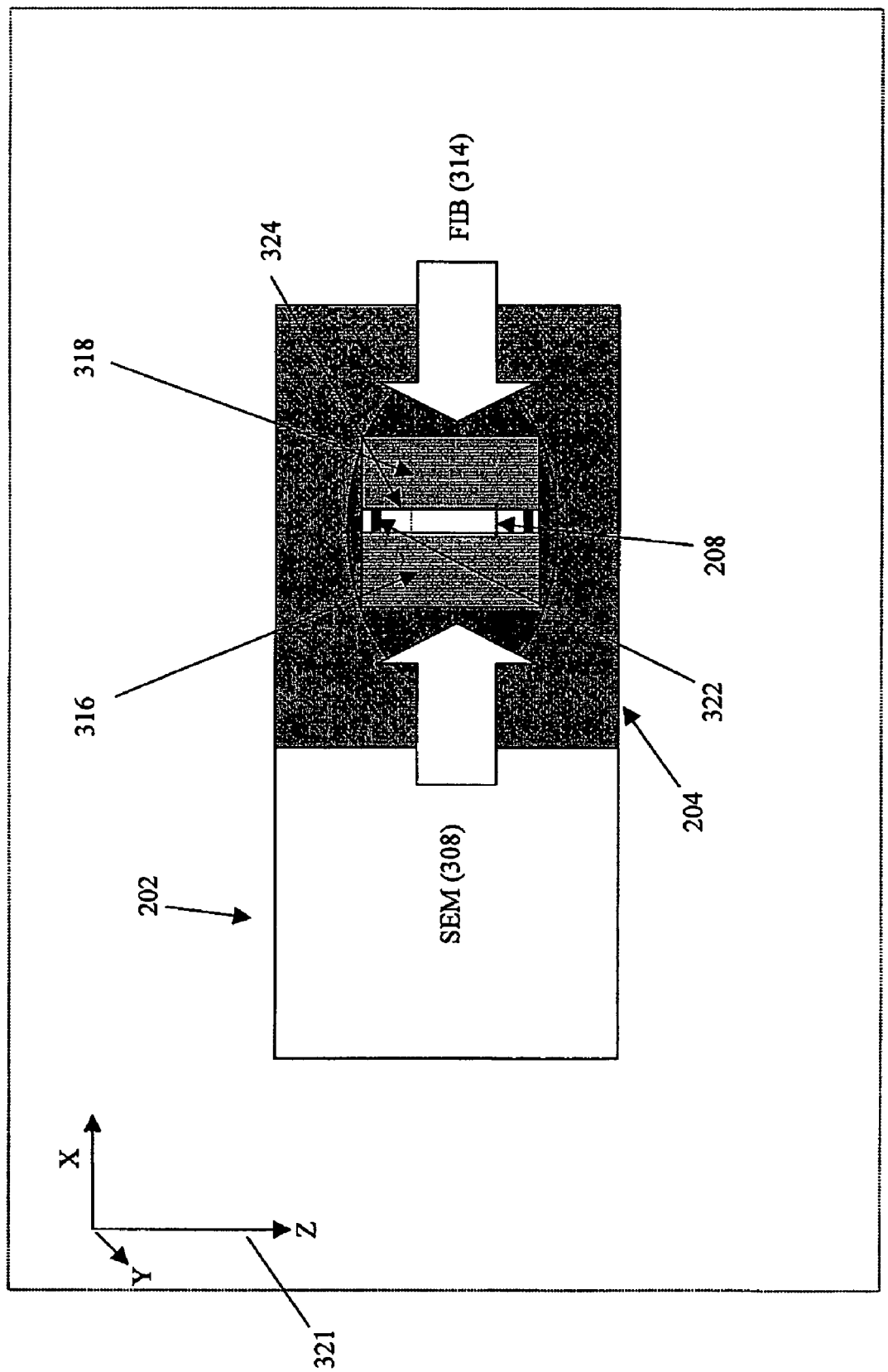

With reference to FIG. 3c, in the example embodiment, the FIB (314) is subsequently utilised to mill two trenches, for example (316) and (318) on each side of the site of interest (208) on the circuit layers (204). The depth of the trenches, (316) and (318), can be determined based on the depth of the site of interest (208) within the circuit layers (204). The depth of the site of interest (208) within the circuit layers (204) may be visualised utilising the SEM (308). After the milling of the two trenches, (316) and (318), the holder (202) is tilted around the z-axis (321), and a U-shaped FIB-milling, as indicated at numeral (322), of the site of interest (208) is performed to cut out a TEM sample (324). In the example embodiment, the dimension of the TEM sample (324) extends beyond the site of interest (208) between the boundaries of the U-shaped FIB-milling, thus avoiding or reducing damage to the site of interest (208) during the U-shaped FIB-milling.

Subsequently, in the example embodiment, the TEM sample (324) may undergo fine polishing and fine milling. This process may thin the TEM sample (324) to be electron-transparent where it will then be suitable for TEM imaging. The resulting TEM sample (324) after processing may then be extracted by an electrostatic probe (not shown) for TEM imaging.

Example results of TEM sample preparation using embodiments of the present invention will now be described.

Figure 4B:
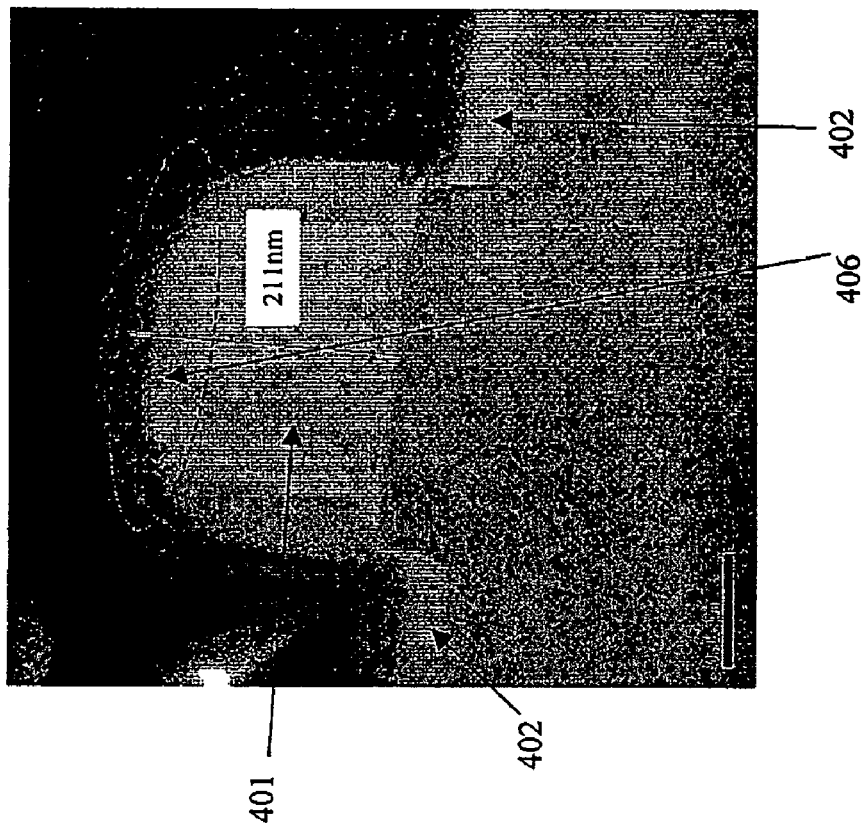
FIGS. 4a and b are TEM images illustrating damage during ion-beam assisted Pt deposition.
Figure 4A:
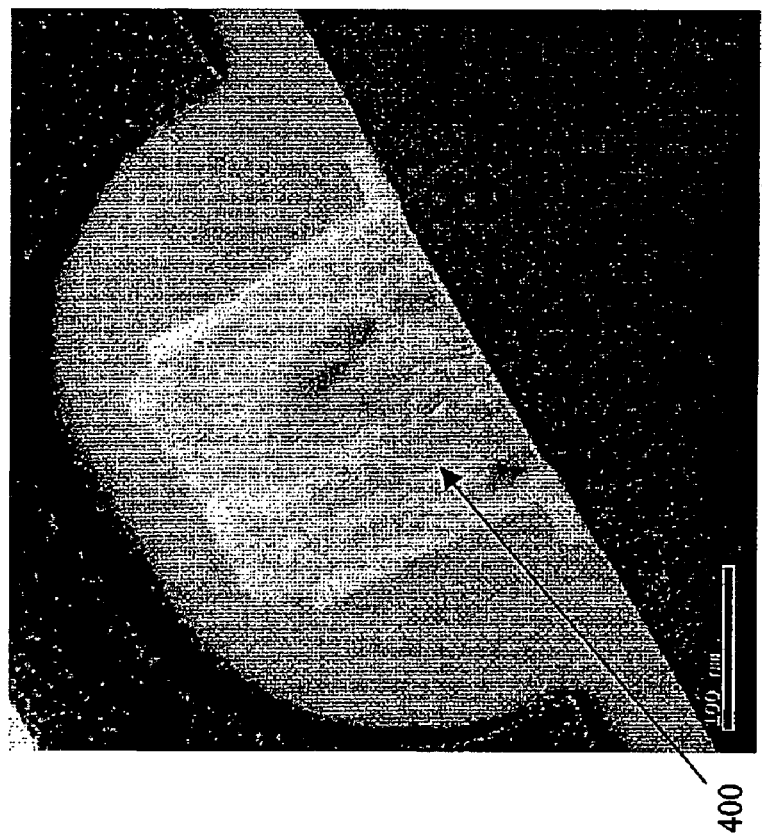

With reference to FIGS. 4a and b, damage observed during Pt deposition using ion-beam deposition of a single protective layer will first be described. More particular, FIG. 4a shows a TEM photo of an "original" poly gate (400), whereas FIG. 4b shows a TEM photo of the poly gate (401) after ion-beam deposition of a single protective layer. A comparison of FIGS. 4a and b illustrates that amorphoriza-tion occurs during ion-beam assisted deposition, in regions (402) adjacent the poly gate (401). Furthermore, changes in the profile of the poly gate (401) are observed, in particular in region (406).

Figure 5B:
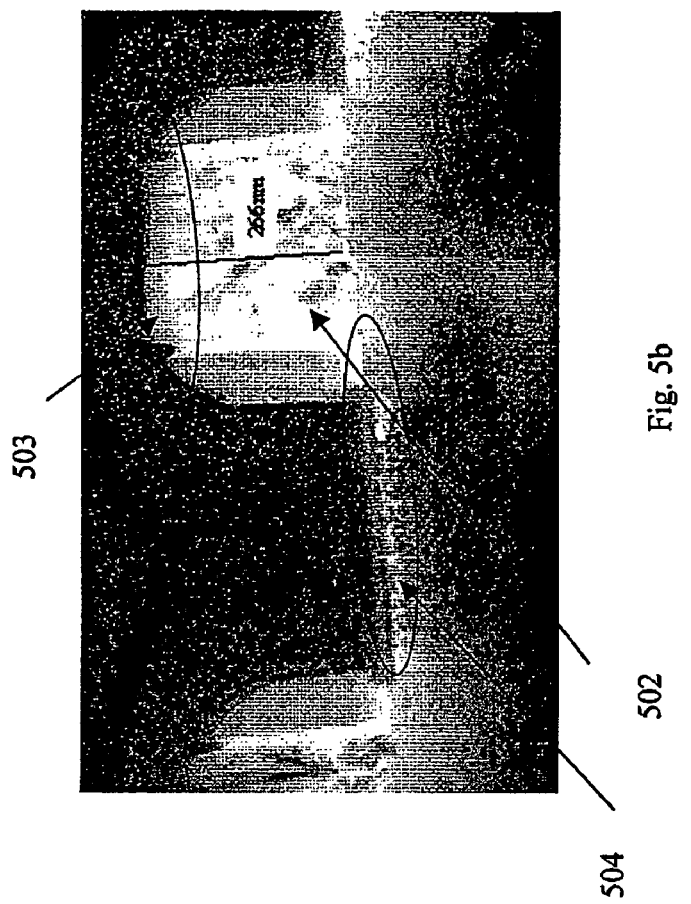
FIGS. 5a and b show TEM images illustrating avoidance of damage through utilising a protective layer structure according to an example embodiment.
Figure 5A:
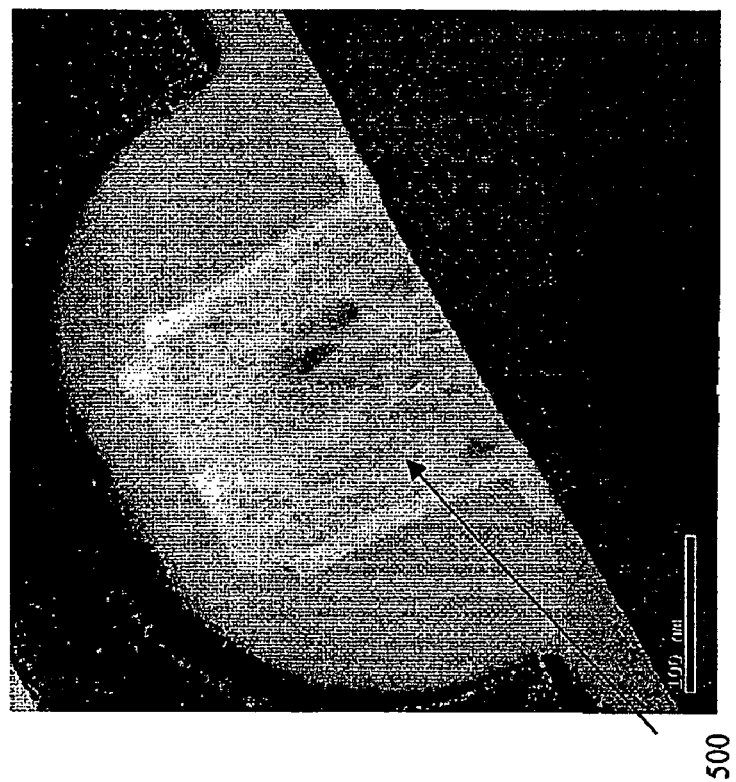

In contrast, FIGS. 5a and b show TEM images of the original profile of an poly gate (500), in FIG. 5a, and the same poly gate indicated and numeral (502) in FIG. 5b after electron-beam assisted Pt deposition. As can be seen from a comparison of FIGS. 5a and b, no damage is detectable on (see e.g. region 503) or adjacent (see e.g. region (504) the poly gate (502).

In another example embodiment, with reference to FIG. 6a, an (unwanted) particle (602) was present on the surface of a wafer (604), visualised by using FIB navigation. It was found that using TEM sample preparation similar to the one described above with reference to FIGS. 3a to c, the particle was still present in a cross-sectional TEM photo (606) shown in FIG. 6b, as indicated as an extra metal line (608) detectable in the TEM photo (606).

Figure 7:
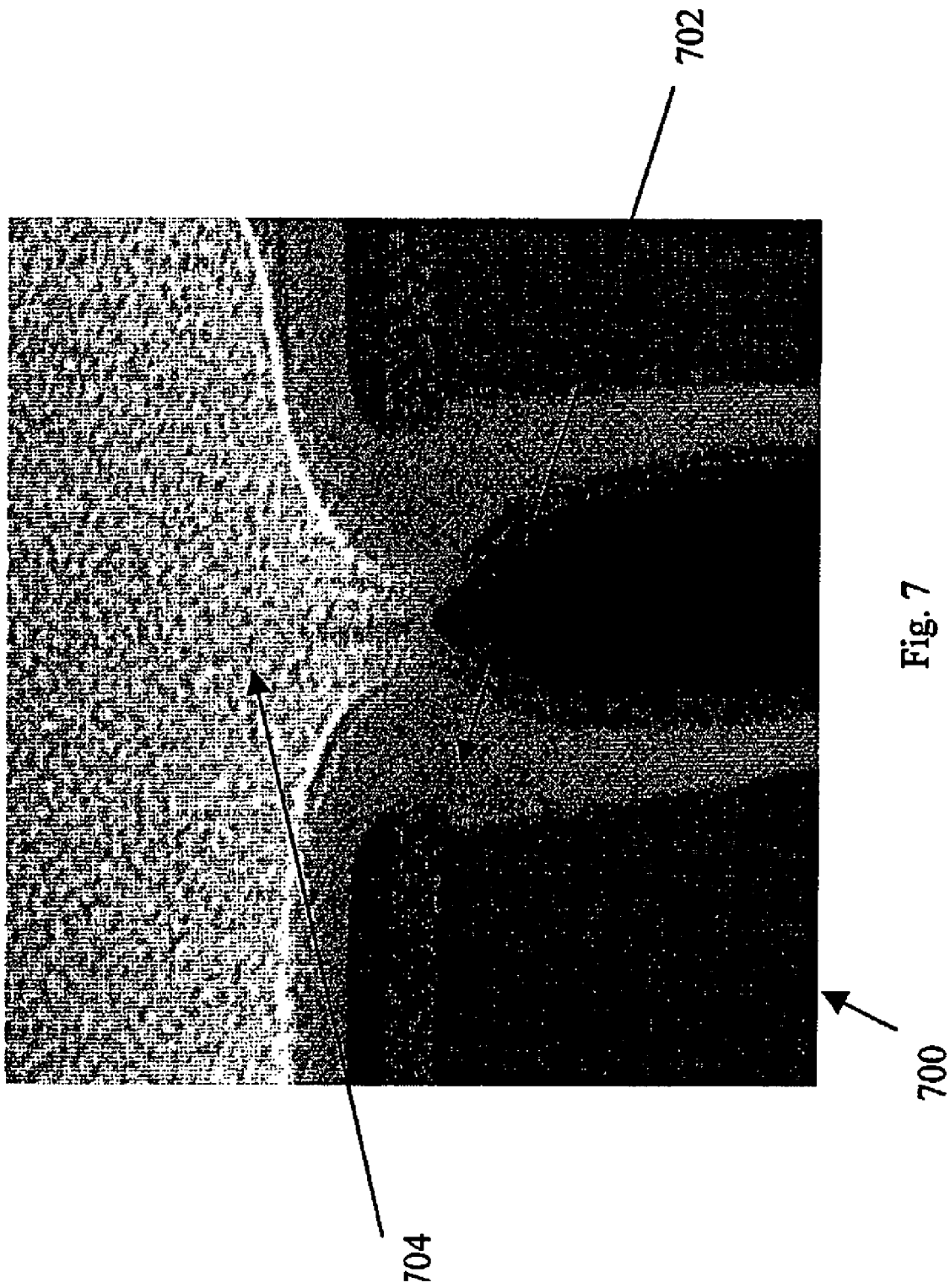
FIG. 7 shows a TEM image of a protective layer structure according to an example embodiment.

In this example embodiment, and with reference to FIG. 7, which shows a higher magnification cross-sectional TEM photo (700) of the wafer (604, FIG. 6a), a two-layered Pt protective coating was applied as follows. A electron beam Pt layer (702) deposited such that a finer Pt particles, less dense layer was formed. An ion beam assisted Pt, nano particle layer (704), was then deposited prior to ion-cutting of the TEM sample.

Figure 8B:
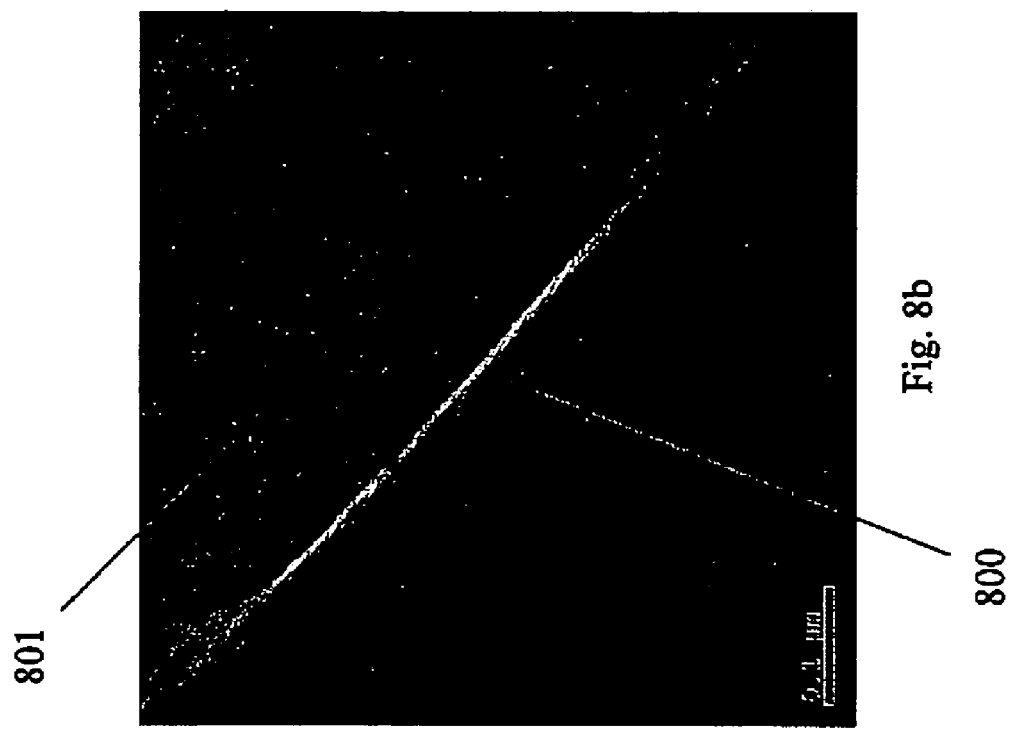
Figure 8A:
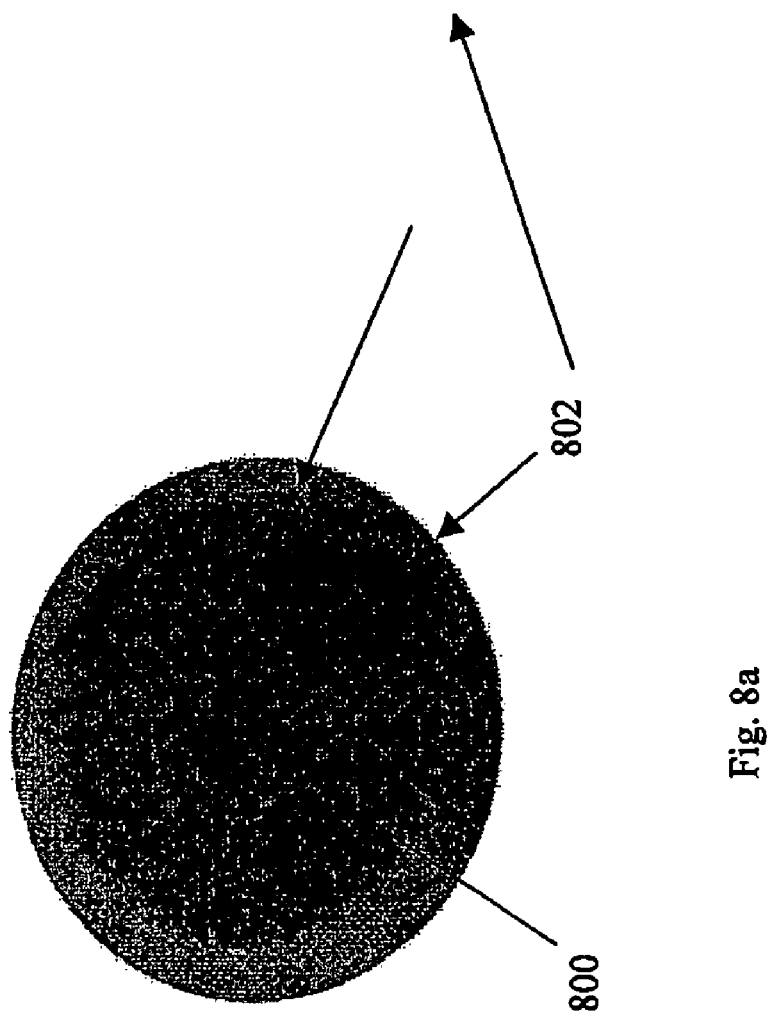

In another example embodiment, with reference to FIG. 8a, an (unwanted) TiN layer (800) was present on the surface of another wafer (802). FIG. 8b shows a cross-sectional electron energy loss spectroscopy (EELS) Ti mapping image of the original wafer (802) profile, showing the presence of the TiN layer (800). For this reference sample, a nitride film (801) was deposited over the TiN layer (800) prior to the sample processing for the EELS Ti mapping, to ensure that the TiN layer (800) would be present.

FIG. 8c shows a similar cross-sectional EELS Ti mapping image, after ion-beam deposition of a Pt layer (804) onto the wafer (802) in the area of the TiN layer. As evident from the image in FIG. 8c, no TiN layer is detectable after ion-beam deposition of the Pt layer (804), demonstrating the sputtering-off of the TiN layer during the ion-beam assisted deposition.

In contrast, FIG. 8d shows a similar cross-sectional Ti mapping image after electron-beam assisted deposition of a first Pt layer over the wafer (802), followed by ion-beam assisted deposition of a second Pt layer over the first layer in the area of the TiN layer (800), in accordance with the process of an example embodiment. As is evident from FIG. 8d, the TiN layer (800) remains detectable, illustrating the suitability of two-layered Pt protective coatings according to embodiments of the present invention in TEM sample preparation for thin film analysis on circuit layer structures. It is noted that in the EELS Ti mapping image, the first and second Pt layers are not resolved separately (together indicated at (806)), as will be appreciated by a person skilled in the art.

Figure 9:
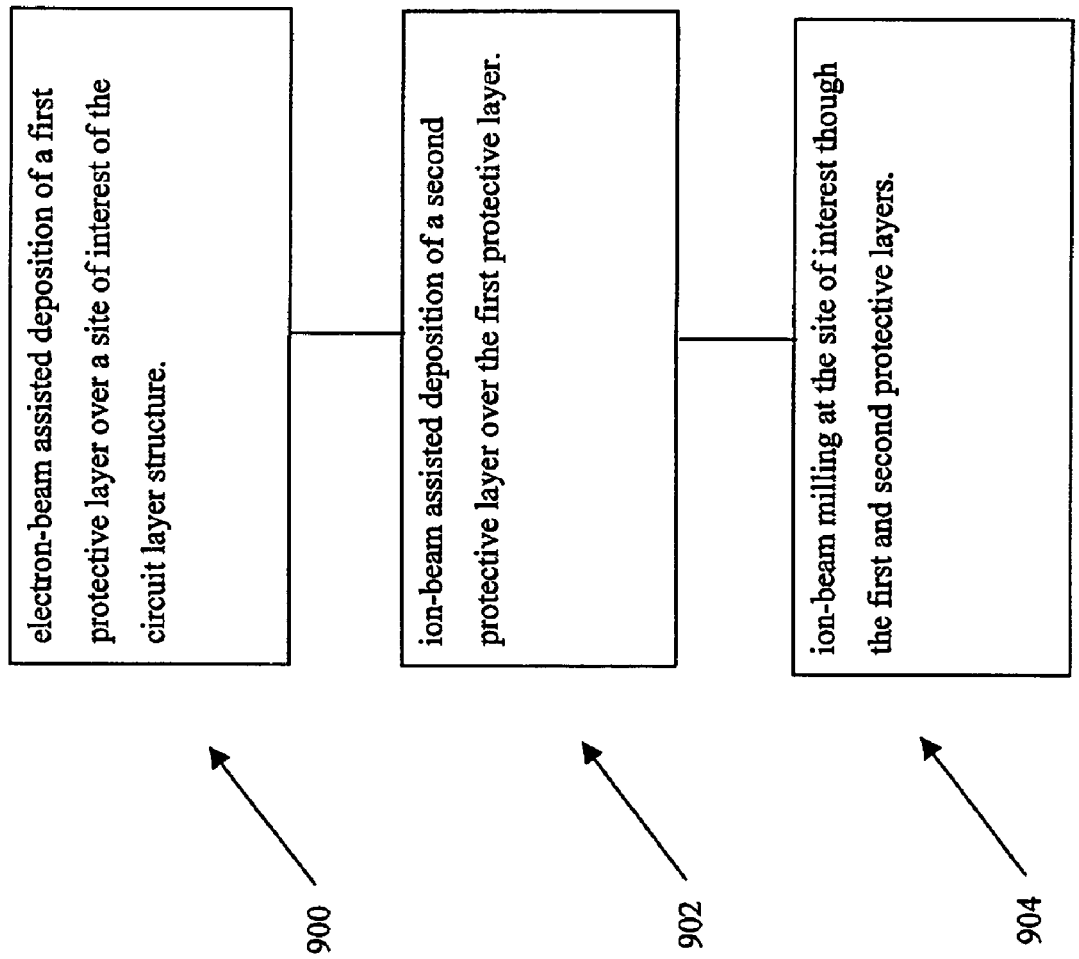
FIG. 9 shows a flow-chart illustrating a method of preparing TEM sample from a circuit layer structure according to an example embodiment.

FIG. 9 shows a flow-chart illustrating a method of TEM sample preparation from a circuit layer structure, according to an example embodiment. At step (900), electron-beam assisted deposition of a first protective layer over a site of interest of the circuit layer structure is performed. At step (902), ion-beam assisted deposition of a second protective layer over the first protective layer is performed. At step (904), ion-beam milling at the site of interest through the first and second protective layers is performed.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A method of TEM sample preparation from a circuit layer structure, the method comprising:
   electron-beam assisted deposition of a first protective layer over a site of interest of the circuit layer structure;
   ion-beam assisted deposition of a second protective layer over the first protective layer; and
   ion-beam milling at the site of interest through the first and second protective layers.

2. The method as claimed in claim 1, further comprising electron-beam assisted deposition of an intermediate protective layer over the first protective layer prior to the ion-beam assisted deposition of the second protective layer over the first and the intermediate protective layers.

3. The method as claimed in claim 1, wherein the first and second protective layers comprise Pt.

4. The method as claimed in claim 3, wherein the first and second protective layers are deposited from methylcyclopentadienyl (trimethyl) platinum $(CH_3C_5H_4)(CH_3)_3$ Pt.

5. The method as claimed in claim 1, wherein the ion-beam comprises Ga ions.

6. The method as claimed in claim 5, wherein a Ga ion-beam acceleration voltage is about 30 kV.

7. The method as claimed in claim 1, wherein an electron-beam voltage is in a range from about 2 to 5 kV.

8. The method as claimed in claim 1, wherein an electron-beam spot size is of the order of tens of nano metres.

9. The method as claimed in claim 1, wherein an electron-beam assisted deposition time is in a range from about 9 to 33 minutes.

10. The method as claimed in claim 1, wherein a thickness of the first protective layer is a range from about 0.036 to 0.7 micrometres, and a thickness of the second protective layer is about 1 micrometre.

11. The method as claimed in claim 1, further comprising tilting the circuit layer structure and performing a substantially U-shaped ion-beam milling to cut out the TEM sample, wherein dimensions of the substantially U-shaped ion-beam milling are chosen such that the ion-beam milling occurs away from the site of interest of the circuit layer structure.

* * * * *